United States Patent
Steinbuchel et al.

(10) Patent No.: US 6,495,152 B2
(45) Date of Patent: Dec. 17, 2002

(54) SULFUR CONTAINING POLYHYDROXYALKANOATE COMPOSITIONS AND METHOD OF PRODUCTION

(75) Inventors: Alexander Steinbuchel, Altenberge (DE); Tina Lütke-Eversloh, Munster (DE); Christian Ewering, Steinfurt (DE)

(73) Assignees: Tepha, Inc., Cambridge, MA (US); Metabolix, Inc., Cambridge, MA (US)

( * ) Notice: Subject to any disclaimer, the term of this patent is extended or adjusted under 35 U.S.C. 154(b) by 0 days.

(21) Appl. No.: 09/932,387

(22) Filed: Aug. 17, 2001

(65) Prior Publication Data

US 2002/0106764 A1 Aug. 8, 2002

Related U.S. Application Data

(60) Provisional application No. 60/226,139, filed on Aug. 18, 2000.

(51) Int. Cl.[7] .................... A01N 25/00; C08G 63/06
(52) U.S. Cl. .................... 424/405; 528/361; 528/364; 528/373; 528/374; 435/130; 435/131; 435/135; 435/136; 435/141; 435/146; 514/512; 514/712
(58) Field of Search .................... 528/361, 364, 528/373, 374; 485/130, 131, 135, 136, 141, 146; 424/405; 514/512, 712

(56) References Cited

U.S. PATENT DOCUMENTS

| | | |
|---|---|---|
| 4,910,145 A | 3/1990 | Holmes et al. |
| 5,245,023 A | 9/1993 | Peoples et al. |
| 5,250,430 A | 10/1993 | Peoples et al. |
| 5,480,794 A | 1/1996 | Peoples et al. |
| 5,512,669 A | 4/1996 | Peoples et al. |
| 5,534,432 A | 7/1996 | Peoples et al. |
| 5,563,239 A | 10/1996 | Hubbs et al. |

FOREIGN PATENT DOCUMENTS

EP 1130043 A2 9/2001

OTHER PUBLICATIONS

Agostini, et al., "Synthesis and Characterization of Poly-β-Hydroxybutyrate. I. Synthesis of Crystalline DL Poly-β-Hydroxybutyrolactone from DL -β-Butyrolactone," *Polym. Sci.* Part A–1, 9:2775–2787 (1971).

Anderson & Dawes, "Occurrence, metabolism, metabolic role and industrial uses of bacterial polyhydroxyalkanoates," *Microbiol. Rev.* 54:450–472 (1990).

Bandiera, et al., "Effect of sodium sulfonate groups on the ionic conductivity of a copolyester of thiodipropionic acid," *Eur. Pol. J.* 33:1679–1683 (1997).

Brandl, et al., "*Pseudomonas oleovorans* as a source of poly(b–hydroxyalkanoates for potential applications as biodegradable polyesters," *Appl. Environ. Microbiol.* 54:1977–1982 (1988).

Byrom, "Miscellaneous Biomaterials," in *Biomaterials* (D. Byrom, ed.) pp. 333–359 (MacMillan Publishers, London 1991).

(List continued on next page.)

*Primary Examiner*—Samuel A. Acquah
(74) *Attorney, Agent, or Firm*—Holland & Knight LLP

(57) ABSTRACT

A class of biopolymer including sulfur in the form of a thioester in the polymer backbone or a thioether in the polymer side chains has been developed. These are preferably produced by fermentation of bacteria with appropriate sulfur containing substrates, which are incorporated by a broad spectrum polyhydroxyalkanoate ("PHA") polymerase. The sulfur-containing PHAs allow various applications and uses in industry. Representative embodiments of the applications of the sulfur-containing PHAs include their uses in the packaging industry, medicine, pharmacy, agriculture or food industry, as active agents or as coatings, packaging, or carriers.

12 Claims, 4 Drawing Sheets

OTHER PUBLICATIONS

Cuebas, et al., "Mitochondrial metabolism of 3–mercaptopropionic acid. Chemical synthesis of 3–mercaptopropionyl coenzyme A and some of its S–acyl derivatives," *J. Biol. Chem.* 260:7330–7336 (1985).

De Smet, et al., "Characterization of intracellular inclusions formed by *Pseudomonas oleovorans* during growth on octane," *J. Bacteriol.* 154:870–78 (1983).

Dubois, et al., "Macromolecular Engineering of Polylactones and Polylactides. 12. Study of the Depolymerization Reactions of Poly (ε–caprolactone) with Functional Aluminum Alkoxide End Groups," *Macromolecules* 26:4407–12 (1993).

Füchtenbusch, et al., "Biosynthesis of novel copolyesters containing 3–hydroxypivalic acid by *Rhodoccus ruber* NCIMB 40126 and related bacteria," *FEMS Microbiol. Lett.* 159:85–92 (1998).

Griebel, et al., "Metabolism of poly–beta–hydroxybutyrate. I. Purification, composition, and properties of native poly–beta–hydroxybutyrate granules from *Bacillus megaterium*," *Biochemistry* 7:3676–3681 (1968).

Gross, et al., "Polymerization if β–monosubstituted–b–propiolactones using trialkylaminimum–water catalytic systems and polymer characterization," *Macromolecules* 21:2657–2668 (1988).

Hocking & Marchessault, "Syndiotactic poly[(R, S)–β–hydroxybutyrate] isolated from methyaluminoxane–catalyzed polymerization," *Polym. Bull.* 30:163–170 (1993).

Hocking & Marchessault, "Biopolyesters" in *Chemistry and Technology of Biodegradable Polymers* (G.J.L. Griffin, ed.) pp. 48–96 (Chapman and Hall, London 1994).

Holmes, "Biologically Produced (R)–3–hydroxyalkanoate Polymers and Copolymers," in D.C. Bassett Ed., "Developments in Crystalline Polymers," Elsevier, London, vol. 2, pp. 1–65, 1988.

Hori, et al., "Ring–Opening Copolymerization of Optically Active β–Butyrolatone with Several Lactones Catalyzed by Distannoxane Complexes: Synthesis of New Biodegradable Polyesters," *Macromolecules* 26:4388–4390 (1993).

Hori, et al., "Ring–Opening Polymerization of Optically Active β–Butyrolactone Using Distannoxane Catalysts: Synthesis of High Molecular Wright Poly(3–hydroxybutyrate)," *Macromolecules* 26:5533–5534 (1993).

Kameyama, et al., "Novel sequence–ordered polymers of transformation of polymer backbone: Quantitative and regioselective insertion of Thiranes into poly(S–aryl thioester)," *Macromol.* 32:1407–1412 (1999).

Kemnitzer, et al., "Preparation of predominantly Syndiotactic Poly(β–hydroxybutyrate) by the Tributylin Methoxide Catalyzed Ring–Opening Polymerization of racemic β–Butyrolactone," *Macromolecules* 26:1221–1229 (1993).

Lafferty et al., "Microbial Production of Poly–β–hydroxybutyric acid," Rehm and Reed, Eds., "Biotechnology" Verlagsgesellschaft, Weinheim, vol. 66, 1988, pp. 135–176.

Le Borgne & Spassky, "Stereoelective polymerization of β–butyrolactone," *Polymer* 30:2312–2319 (1989).

Lemoigne and Roukhelman, "Fermetation β–Hydroxybutyrique Caracterisation et Evolution Des Produits de Deshydration et de Polymerisation de L'acide β–Dehydroxybutyrique," *Annales des fermentations*, 5:527–36 (1925).

Müh, et al., "PHA synthase from *chromatium vinosum:* cysteine 149 is involved in covalent catalysis," *Bioche.* 38:826–837 (1999).

Müller & Seebach, "Poly(hydroxyalkanoates): A Fifth Class of Physiologically Important Organic Biopolymers," *Angew. Chem. Int. Ed. Engl.* 32:477–502 (1993).

Nakamura et al., "Biosynthesis and characteristics of bacterial poly(3–hydroxybutyrate–co–3–hydroxypropionate)," *Macromol. Rep.* A28, 15–24 (1991)).

Pedrós–Alio et al., "The influence of poly–β–hydroxybutyrate accumulation on cell volume and buoyant density in *Alcaligenes eutrophus*," *Arch. Microbiol.* 143:178–184 (1985).

Rehm & Steinbüchel, "Biochemical and genetic analysis of PHA synthases and other proteins required for PHA synthesis," *Int. J. Biol. Macromol.* 25:3–19 (1999).

Sabbagh, et al., "3–Mercaptopropionic acid, a potent inhibitor of fatty acid oxidation in rat heart mitochondria," *J. Biol. Chem.* 260:7337–7342 (1985).

Schlegel, et al., "Ein submersverfahren zur kultur wasserstoffoxydierender bakterien: Wachstumsphysiologische untersuchungen," *Arch. Mikrobiol.* 38:209–222 (1961).

Skrede et al, "Thia fatty acids, metabolism and metabolic effects" in *Biochim Biophys Acta* 1344:115–31 (1997).

Steinbüchel & Valentin, "Diversity of microbial polyhydroxyalkanoic acids" *FEMS Microbiol Lett* 128:219–228 (1995).

Steinbüchel, et al., "A *Pseudomonas* strain accumulating polyesters of 3–hydroxybutyric acid and medium–chain–length 3–hydroxyalkanoic acids," *Appl. Microbiol. Biotechnol.* 37:691–97 (1992).

Steinbüchel, "Polyhydroxyalkanoic Acids," in Byrom Ed., "Biomaterials" MacMillan Publishers, London, 1991, pp. 123–213.

Tanahashi & Doi, "Thermal Properties and Steroregularity of Poly(3–hydroxybutyrate) Prepared from optically Active β–Butyrolactone with a Zinc–Based Catalyst," *Macromolecules* 24:5732–5733 (1991).

Wallen and Rohwedder, "Poly–β–hydroxyalakaonate from Activated Sludge," *Environ. Sci. Technol.* 8:576–79 (1974).

Williams & Peoples, "Biodegradable plastics from plants," *Chemtech* 26:38–44 (1996).

Wodzinska, et al., "Polyhydroxybutyrate synthase: Evidence for covalent catalysis," *J. Am. Chem. Soc.* 118:6319–6320 (1996).

Worsey & Williams, "Metabolism of toluene by *Pseudomonas putida (arvilla)* mt–2: evidence for a new function of the TOL plasmid" *J Bacteriol* 124:7–13 (1975).

Xie, et al., "Ring–opening Polymerization of β–butyrolactone by Thermophilic Lipases," *Macromolecules* 30:6997–6998 (1997).

Lütke–Eversloh et al., "Identification of a new class of biopolymer: Bacterial synthesis of a sulphur–containing polymer with thioester linkages," *Microbiology* 147 (1): 11–19 (2001).

Lütke–Eversloh et al., "List of submitted abstracts," *The 8th International Symposium on Biological Polyesters* (2000).

Takagi et al., "Biosynthesis of polyhydroxyalkanoate with a thiophenoxy side group obtained from Pseudomonas putida," *Macromolecules* 32: 8315–8318 (1999).

SULFUR CONTAINING POLYHYDROXYALKANOATE COMPOSITIONS AND METHOD OF PRODUCTION

CROSS-REFERENCE TO RELATED APPLICATIONS

Priority is claimed to U.S. Provisional application Serial No. 60/226,139, filed Aug. 18, 2000, the teachings of which are incorporated herein.

BACKGROUND OF THE INVENTION

The present invention is generally in the field of biopolymers, and in particular describes a class of polythioesters which can be produced by bacterial fermentation.

Polymers are the most abundant molecules in living matter. There are seven general classes of biopolymers are distinguished: polynucleotides, polyamides, polysaccharides, polyisoprenes, lignin, polyphosphate and polyhydroxyalkanoates, PHA (Müller & Seebach, 1993) (Table 1). Poly(3-hydroxybutyrate), PHB, belongs to the latter class as a wide spread bacterial storage compound and was already observed in 1926 as hydrophobic inclusions in the cytoplasm of Bacillus megaterium (Lemoigne, 1926). Today many genera of bacteria are known to accumulate PHAs as energy and carbon source mostly under restricted growth conditions, e.g. oxygen- or nitrogen-limitation (Anderson & Dawes, 1990; Steinbüchel, 1991).

Polyhydroxyalkanoates (PHAs) are polymers with repeating hydroxy acid monomeric units. PHAs have been reviewed in several publications, including Byrom, "Miscellaneous Biomaterials," in Biomaterials (D. Byrom, ed.) pp. 333–59 (MacMillan Publishers, London 1991); Hocking and Marchessault, "Biopolyesters" in Chemistry and Technology of Biodegradable Polymers (G. J. L. Griffin, ed.) pp. 48–96 (Chapman and Hall, London 1994); Müller and Seebach, Angew. Chem. Int. Ed. Engl., 32:477–502 (1993); Steinbüchel, "Polyhydroxyalkanoic Acids," in Biomaterials (D. Byrom, ed.) pp. 123–213 (MacMillan Publishers, London 1991); and Williams and Peoples, CHEMTECH, 26:38–44 (1996).

A wide range of bacteria are known to accumulate polyhydroxyalkanoates (PHA) as intracellular storage compounds. Due to the properties of these polymers as biodegradable thermoplastics, and elastomers they have attracted much interest and are considered for various technical applications in industry, medicine, agriculture and other areas (Anderson, A. J. & Dawes, E. A., Microbiol. Rev. 54, 450–472 (1990); Steinbüchel, 1991).

Several types of polyhydroxyalkanoates are formed in nature by various organisms in response to environmental stress. These PHAs can be broadly divided into three groups according to the length of their pendant groups and their respective biosynthetic pathways. Relatively short pendant groups include the $C_{3-5}$ hydroxy acids, whereas relatively long pendant groups include $C_{6-14}$ hydroxy acids.

There are three major types of naturally occurring PHAs. The first type includes only relatively short hydroxy acid monomeric units. The second type include both relatively short and relatively long hydroxy acid monomeric units. The third type includes only relatively long hydroxy acid monomeric units. Those with short pendant groups, such as polyhydroxybutyrate (PHB), a homopolymer of R-3-hydroxybutyric acid (R-3HB) units, are highly crystalline thermoplastic materials (Lemoigne and Roukhelman, Annales des fermentations, 5:527–36 (1925)). PHAs containing the short R-3HB units randomly polymerized with much longer pendant group hydroxy acid units were first reported in the early seventies (Wallen and Rohwedder, Environ. Sci. Technol., 8:576–79 (1974)). A number of microorganisms which specifically produce copolymers of R-3HB with these longer pendant group hydroxy acid units are also known and belong to this second group (Steinbüchel and Wiese, Appl. Microbiol Biotechnol., 37:691–97 (1992)). In the early 1980's, a research group in The Netherlands identified the third group of PHAs, which contains predominantly longer pendant group hydroxy acids (De Smet, et al., J. Bacteriol., 154:870–78 (1983)).

PHAs may constitute up to 90% of the dry cell weight of bacteria, and are found as discrete granules inside the bacterial cells. These PHA granules accumulate in response to nutrient limitation and serve as carbon and energy reserve materials. Distinct pathways are used by microorganisms to produce each group of these polymers. One of these pathways leading to the short pendant group polyhydroxyalkanoates (SPGPHAs) involves three enzymes: thiolase, reductase, and PHB synthase (sometimes called polymerase). Using this pathway, the homopolymer PHB is synthesized by condensation of two molecules of acetyl-Coenzyme A to give acetoacetyl-Coenzyme A, followed by reduction of this intermediate to R-3-hydroxybutyryl-Coenzyme A, and subsequent polymerization. The last

TABLE 1

Eight classes of biopolymers and characteristics of their biosynthesis and occurrence

| Class | Template-dependent synthesis | Substrate of the polymerase | Synthesis in | |
|---|---|---|---|---|
| | | | Prokaryote | Eukaryote |
| Nucleic acids | yes | DNTPs, NTPs | yes | yes |
| Proteins and | yes | aminoacyl-tRNAs | yes | yes |
| Polyaminoacids | no | amino acids | yes | yes |
| Polysaccharides | no | Sugar-NDP, Sucrose | yes | yes |
| Polyhydroxyalkanoate | no | Hydroxyacyl Co A | yes | no |
| Polythiesters | no | Mercaptoacyl Co A | yes | no |
| Polyphosphate | no | ATP | yes | yes |
| Polyisoprenoids | no | A* | no | only plants |
| Lignin | no | B* | no | only plants |

*A: Isopentenylpyrophosphate;
B: Radicalic intermediates.

enzyme in this pathway, the synthase, has a substrate specificity that can accommodate $C_{3-5}$ monomeric units, including R-4-hydroxy acid and R-5-hydroxy acid units. This biosynthetic pathway is found, for example, in the bacteria *Zoogloea ramigera* and *Alcaligenes eutrophus*.

The biosynthetic pathway which is used to make the third group of PHAs, long pendant group polyhydroxyalkanoates (LPGPHAs), is still partly unknown. However, it is currently thought that the monomeric hydroxyacyl units leading to the LPGPHAs are derived by the α-oxidation of fatty acids and the fatty acid pathway. The R-3-hydroxyacyl-Coenzyme substrates resulting from these routes are then polymerized by PHA synthases (sometimes called polymerases) that have substrate specificities favoring the larger monomeric units in the $C_{6-14}$ range. LPGPHAs are produced, for example, by Pseudomonads.

The second group of PHAs containing both short R-3HB units and longer pendant group monomers are believed to utilize both the pathways to provide the hydroxy acid monomers. The latter are then polymerized by PHA synthases able to accept these units.

Roughly 100 different types of PHAs have been produced by fermentation methods so far (Steinbüchel and Valentin, *FEMS Microbiol., Lett.*, 128:219–28 (1995)). A number of these PHAs contain functionalized pendant groups such as esters, double bonds, alkoxy, aromatic, halogens, and hydroxy groups. Transgenic systems for producing PHAs in both microorganism and plants, as well as enzymatic methods for PHA synthesis, are reviewed by Williams and Peoples, *CHEMTECH*, 26:38–44 (1996).

Two PHAs belonging to the first group, polyhydroxybutyrate (PHB) and polyhydroxybutyrate-co-valerate (PHBV), have been extensively studied. PHBV is a copolymer of R-3HB units with 5–24% R-3-hydroxyvaleric acid (R-3HV), and is known commercially as Biopol™ (supplied by ICI/Zeneca). These polymers are natural thermoplastics which can be processed using conventional polymer technology and which have industrially useful properties, such as biodegradability in soil and marine environments and good barrier properties. They are characterized by melting points which range from 130 to 180° C., and extensions-to-break of 8 to 42% (see Zeneca Promotional Literature, Billingham, UK 1993).

So far, more than 130 different hydroxyalkanoic acids have been described as constituents of PHAs, comprising 3-, 4-, 5-, and 6-hydroxyalkanoic acids of various chain length. The pendant alkyl side chain can in addition contain various constituents (for review see Steinbüchel & Valentin, 1995). Whereas the large variety of PHA constituents refers almost exclusively to the modified side chains in the β-position of the hydroxyalkanoic acids, PHAs with modified backbones are rare. Examples are 2-methyl-3-hydroxybutyric acid and 3-hydroxypivalic acid, which have been identified as PHA constituents resulting in polymer chains with one or two methyl groups, respectively, in the backbone (Satho et al., (1992) *Wat. Sci. Technol.* 26, 933–942; Füchtenbusch et al., (1998) *FEMS Microbiol. Lett.* 159, 85–92).

Bacteria synthesize PHAs from coenzyme A thioesters of the respective hydroxyalkanoic acid and are able to produce a wide range of different PHAs due to the rather unspecific PHA synthases that catalyze the polymerization reaction. In 1974, 3-hydroxyvaleric acid and 3-hydroxyhexanoic acid were identified as additional constituents of these bacterial polyesters (Wallen & Rohwedder, 1974). Only a few polyesters can be obtained from simple and abundantly available carbon sources, e.g. glucose. The large variety of PHAs comprises 3-, 4-, 5-, and 6-hydroxyalkanoic acids of varying chain length, possibly containing additional methyl or other alkyl groups, double bonds, or different substituents at various positions of the hydroxyalkanoic acid and is often based on the feeding of suitable precursor substrates, which exhibit chemical structures related to the PHA constituents (Steinbüchel & Valentin, 1995).

It is an object of the present invention to provide a class of polyhydroxyalkanoates which include a thioester bond in the polymer backbone or a thioether bond in the polymer side chains.

It is a further object of the present invention to provide a means for producing polyhydroxyalkanoates which include a thioester bond or thioether bond.

SUMMARY OF THE INVENTION

Biopolymers including sulfur in the form of a thioester in the polymer backbone or a thioether in the polymer side chains have been developed. These are preferably produced by fermentation of bacteria with appropriate sulfur containing substrates, which are incorporated by a broad spectrum PHA polymerase.

As demonstrated by example 1, a hitherto unknown copolymer that contains sulfur in the backbone linking 3-mercaptopropionic acid and 3-hydroxybutyric acid by thioester linkages was synthesized by *R. eutropha*. Besides proteins and some complex polysaccharides, this is the first demonstration of the biosynthesis of a polymer containing sulfur. The copolymer contributed up to 19% of the cellular dry weight and consisted of up to 43 mol% of 3-mercaptopropionic acid.

As demonstrated by example 2, a hitherto unknown copolymer that contains sulfur in the backbone linking 3-hydroxybutyrate and 3-mercaptobutyrate by thioester linkages was synthesized by the polyhydroxyalkanoate-(PHA) accumulating bacterium *R. eutropha*, when 3-mercaptobutyric acid was fed as carbon source in addition to gluconate. The chemical structure of this polymer was confirmed by gas chromatography/mass spectrometry, infrared spectroscopy, $^1$H- and $^{13}$C-nuclear magnetic resonance spectroscopy, and elemental sulfur analysis.

As demonstrated by example 3, in the presence of PTO in the medium, *R. eutropha* PHB-4 pBBR1 : phaC 1 synthesized a hitherto unknown polyester including exclusively 3-hydroxypropylthiobutyrate, 3-hydroxypropylthiohexanoate, and 3-hydroxypropylthiooctanoate as polymer constituents, poly (3HPTB-co-3HPTHx-co-3HPTO). Larger amounts of poly (3HPTB-co-3HPTHx-co-3HPTO) can also be produced via biological engineering.

The sulfur-containing PHAs allow various applications and uses in industry. Representative embodiments of the applications of the sulfur-containing PHAs include their uses in the packaging industry, medicine, pharmacy, agriculture or food industry, as active agents or as coatings, packaging, or carriers.

In one preferred embodiment, the sulfur-containing PHAs can be used as an anti-bacterial agent, an anti-viral agent, or an anti-fungal agent. In one most preferred embodiment, the sulfur-containing PHAs can be used as anti-bacterial coatings.

In another preferred embodiment, the sulfur-containing PHAs are used as electrolytes.

DETAILED DESCRIPTION OF THE INVENTION

Figure 1:
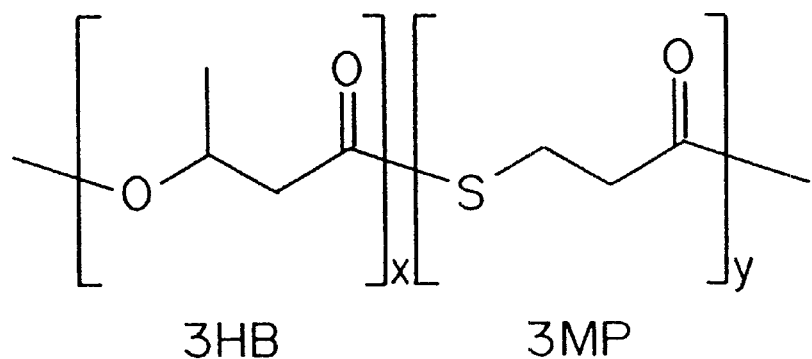
FIG. 1 is the structural formula of poly(3HB-co-3MP).

Abbreviations: PHA, polyhydroxyalkanoate; 3HB, 3-hydroxybutyrate; PHB, Poly(3-hydroxybutyrate); 3MB, 3-mercaptobutyrate (as constituent of the polymer); Poly (3HB-co-3MP), Poly(3-hydroxybutyrate-co-3-mercaptopropionate); 3HP, 3-hydroxypropionate; 3MP, 3-Mercaptopropionic acid (as constituent of the polymer); TDP, 3,3'-thiodipropionic acid. ATA, alkylthioalkanoic acids; ATCC, American type culture collection; BTV, butylthiovaleric acid; DSM, Deutsche Sammlung für Mikroorganismen und Zellkulturen; 3HD, 3-hydroxydecanoate; 3HDD, 3-hydroxydodecanoate; 3HHp, 3-hydroxyheptanoate; 3HHx, 3-hydroxyhexanoate; 3HN, 3-hydroxynonanoate; 3HO, 3-hydroxyoctanoate; 3HPTB, 3-hydroxypropylthiobutyrate; 3HPTHx, 3-hydroxypropylthiohexanoate; 3HPTO, 3-hydroxypropylthiooctanoate; 3HUD, 3-hydroxyundecanoate; MCL, medium chain length; OTHx, octylthiohexanoic acid; PHA, polyhydroxyalkanoate; poly (3HB), poly(3-hydroxybutyrate); poly(3HATA), poly(3-hydroxyalkylthioalkanoate); poly(3HPTA), poly(3-hydroxypropylthioalkanoate); PTB, propylthiobutyric acid; PTE, polythioester; PTHx, propylthiohexanoic acid; PTO, propylthiooctanoic acid; PTP, propylthiopropionic acid; PTUD, propylthioundecanoic acid; SCL, short chain length; TMSD, (trimethylsilyl)diazomethane.

1. Sulfur-Containing PHA Formulas

The PHAs as described herein can be in the form of homopolymers, heteropolymers, block copolymers, or random copolymers. They include sulfur in the form of a thioesters in the polymer backbone or a thioether in the polymer side chain. The polymers can have a formula which has a sulfur atom in the 2-, 3-, or 4- position relative to the carboxylic carbon in its monomeric unit.

In one embodiment, the molecular weight of the polymers is preferably between 300 and $10^7$, and, more preferably, between 10,000 and 10,000,000 Daltons. The PHAs preferably contain one or more units, more preferably between 10 and 100,000 and most preferably between 100 and 30,000 units of the following formula:

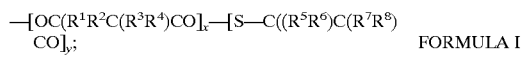

FORMULA I wherein x and y are an integer, for example, between 1 and 15, preferably between 1 and 4; and wherein $R^1$, $R^2$, $R^3$, $R^4$, $R^5$, $R^6$, $R^7$, and $R^8$ are independently selected from hydrogen, methyl, $C_{2-15}$ straight, branched or cyclic alkyl, alkenyl or alkynyl groups, alkaryl groups, aralkyl groups, heteroalkyl groups, heteroaryl groups, hydroxy groups, thiol groups, disulfides, ether groups, thioether groups, ester groups, carboxylic acid groups, amine groups, amide groups, halogens, nitrogen-substituted radicals; and/or oxygen-substituted radicals.

Another preferred form of the PHAs disclosed herein contain one or more units, more preferably between 10 and 100,000 and most preferably between 100 and 30,000 units of the following formula:

Formula II

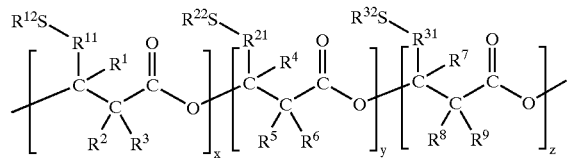

wherein x, y and z are integers, for example, 0 and 15, preferably between 0 and 4, with the proviso that x+y+z>1;

wherein $R^1$, $R^2$, $R^3$, $R^4$, $R^5$, $R^6$, $R^7$, $R^8$ and $R^9$ are independently selected from hydrogen, methyl, $C_{2-15}$ straight, branched or cyclic alkyl, alkenyl or alkynyl groups, alkaryl groups, aralkyl groups, heteroalkyl groups, heteroaryl groups, hydroxy groups, thiol groups, disulfides, ether groups, thioether groups, ester groups, carboxylic acid groups, amine groups, amide groups, halogens, nitrogen-substituted radicals; and/or oxygen-substituted radicals;

wherein $R^{11}$, $R^{21}$, and $R^{31}$ are di-radical groups which are independently selected from substituted or unsubstituted methylene, $C_{2-15}$ straight, branched or cyclic alkyl, alkenyl or alkynyl groups, alkaryl groups, aralkyl groups, heteroalkyl groups, and heteroaryl groups; and wherein $R^{12}$, $R^{22}$, and $R^{32}$ are independently hydrogen, methyl, $C_{2-15}$ straight, branched or cyclic alkyl, alkenyl or alkynyl groups, alkaryl groups, aralkyl groups, heteroalkyl groups, and heteroaryl groups.

Suitable monomeric units include 2-, 3-, or 4-hydroxyalkanoic acids, 2-, 3-, or 4-thioalkanoic acids, alkylthio, alkenylthio, alkynylthio, arylthio, or cycloalkylthioalkanoic acids. Representative monomeric units include hydroxybutyrate, hydroxyvalerate, hydroxyhexanoate, hydroxyheptanoate, hydroxyoctanoate, hydroxynonanoate, hydroxydecanoate, hydroxyundecanoate, hydroxydodecanoate, 3-mercaptopropionic acid, 3,3'-thiodipropionic acid, propylthioundecanoic acid (PTUD), propylthiooctanoic acid (PTO), propylthiohexanoic acid (PTHx), propylthiobutyric acid (PTB), propylthiopropionic acid (PTP), butylthiovaleric acid (BTV), and octylthiohexanoic acid (OTHx).

Although described herein primarily with reference to the polyhydroxyalkanoate polymers, it is understood that these polymers may be blended with other polymers, and/or co-polymerized with monomers or other polymers to form polyhydroxyalkanoate copolymers.

2. Biosynthetic Pathways of Sulfur-containing Polymers

PHAs can be synthesized via well documented pathways in the art. For example, PHAs can be synthesized through butyrate fermentation pathway, fatty acid biosynthetic pathway, or fatty acid oxidative metabolic pathway (see, e.g., Nawrath et al., Targeting of the polyhydroxybutyrate biosynthetic pathway to the plastids of Arabidopsis thaliana results in high levels of polymer accumulation" in Proc Natl Acad Sci U S A. 91(26):12760–4 (1994)). In the synthesis of sulfur-containing PHAs, the peculiarity of the sulfur chemistry may have some implications in the biosynthetic the PHAs.

Considerations of the Biosynthetic Pathway of Thioester-containing Polymers

Figure 3:
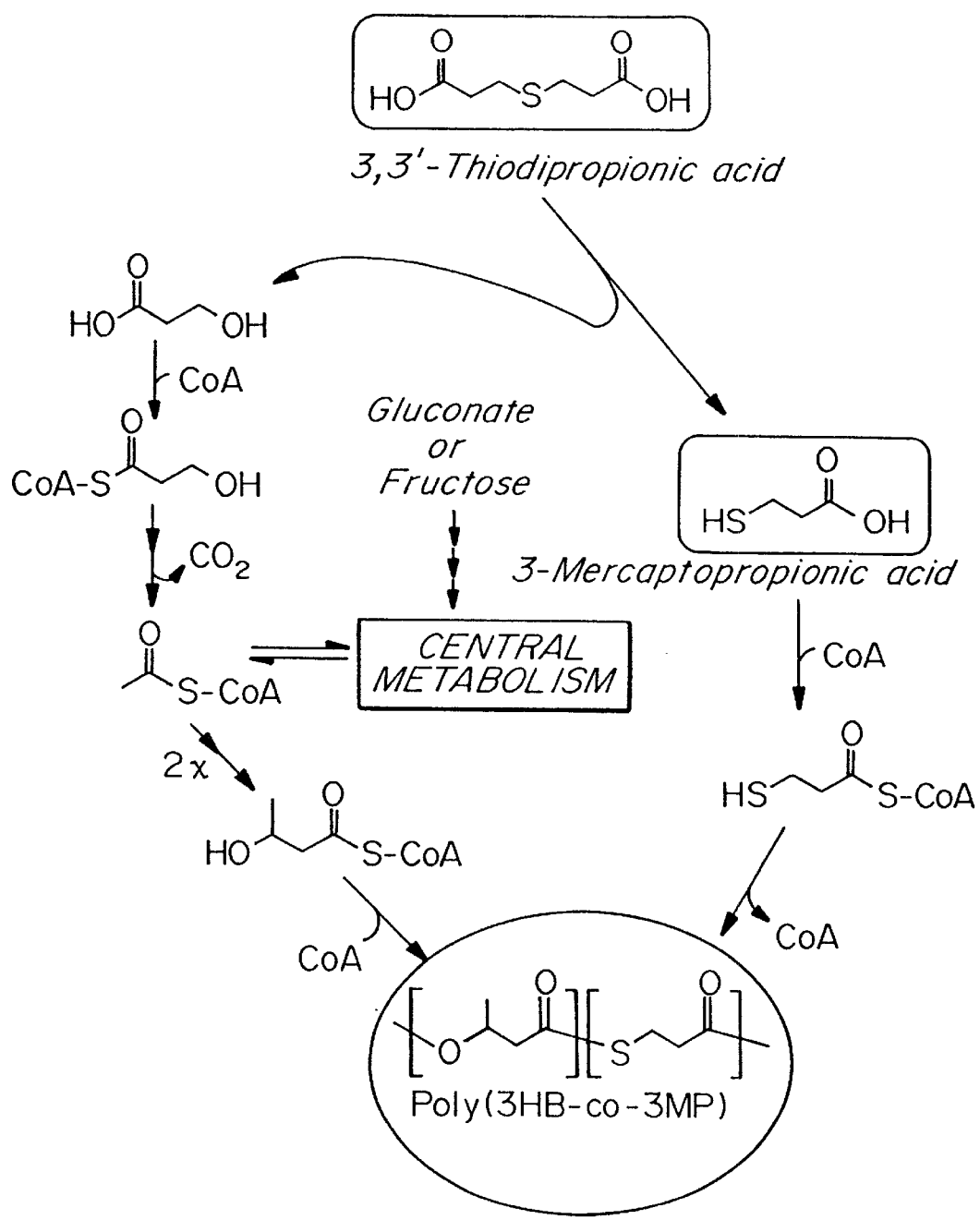
FIG. 3 is a schematic of the putative pathway for the biosynthesis of poly(3HB-co-3MP) from 3,3'-thiodipropionic acid or 3-mercaptopropionic acid in *R. eutropha*.

As a prerequisite for PHA biosynthesis, the provided carbon source must be transported into the cells, and is subsequently metabolized via central pathways (e.g., fatty acid β-oxidation, citric acid cycle, fatty acid de novo synthesis) or special pathways to a hydroxyacyl coenzyme A thioester (Anderson & Dawes, 1990). In the simplest way, a hydroxyalkanoic acid can be directly activated to the corresponding coenzyme A thioester, which serves as substrate for the PHA synthase, the key enzyme of PHA synthesis catalyzing the polymerization reaction. For example, uptake and activation of 3-mercaptopropionic acid to form 3MP-CoA and subsequent incorporation into a sulfur-containing polymer such as poly(3HB-co-3MP) are most likely to occur in R. eutropha if 3-mercaptopropionic acid is provided as carbon source (FIG. 3). The conversion of 3MP to 3MP-CoA has been shown for example in rat heart mitochondria, where it is catalyzed by the medium-chain acyl-CoA synthase (Cuebas et al., *J. Biol. Chem.* 260:7330–7336 (1985)). Inhibitory effects on enzymes of the beta-oxidation in mitochondria caused by 3MP-CoA have been described (Sabbagh et al., *J. Biol. Chem.* 260:7337–7342 (1985)), possibly explaining the growth inhibition of R. eutropha and other bacteria due to higher concentrations of 3-mercaptopropionic acid in the media.

Regarding the catalytic mechanism of PHA synthases, the hydroxy group of the constituent, which will be incorporated, provides a free electron pair for the nucleophilic attack at the carbonyl carbon atom of the nascent polymer chain (Griebel et al., *Biochemistry* 7:3676–3681 (1968); Wodzinska et al., *J. Am. Chem. Soc.* 118:6319–6320 (1996); Müh et al., *Bioche.* 38:826–837 (1999)). A sulfhydryl group in β-position of the substrate also fulfils this prerequisite for the PHA synthase, because 3MB can be incorporated into the polymer resulting in a thioester linkage. Due to the fact that 3MP and 3MB were identified as polymer constituents, they represent a group of substrates for polymer synthesis catalyzed by PHA synthases: β-mercaptoalkanoic acids (MA), corresponding to the oxygen analogues of β-hydroxyalkanoic acids (HA).

Considerations on the Metabolic Pathways for Thioether-containing Polymer

The substrates, ATAs, are probably activated to the corresponding coenzyme A thioesters by an acyl-CoA synthase or a CoA transferase and are subsequently further catabolized via the fatty acid β-oxidation pathway. Conversion of ATAs (thia fatty acids) to the corresponding CoA thioesters have been shown to occur for example in rat hepatocysts (Skrede et al. 1997). However, due to the thioether bonds, the derivatives can not be completely degraded. For example, PTO is first activated to the corresponding coenzyme A thioester, and the resulting PTO-CoA thioester is then metabolized to 3HPTO-CoA, which was incorporated into PHA catalyzed by the P. mendocina PHA synthase. Furthermore, the next intermediate of the β-oxidation cycle, which is 3-ketopropylthiooctanoic acid, is cleaved by a β-ketothiolase resulting subsequently in the formation of 3HPTHx-CoA, which was also incorporated into PHAs. The next cycle of the β-oxidation provides then 3HPTB, which was also incorporated.

3. Preparation of Sulfur Containing PHAs

Methods which can be used for producing PHA polymers from microorganisms which naturally produce polyhydroxyalkanoates are described in U.S. Pat. No. 4,910,145 to Holmes, et al.; Byrom, D., "Miscellaneous Biomaterials," in D. Byrom, Ed., "Biomaterials" MacMillan Publishers, London, 1991, pp. 333–59; Hocking, P. J. and Marchessault, R. H. (1994); Holmes, P. A., "Biologically Produced (R)-3-hydroxyalkanoate Polymers and Copolymers," in D.C. Bassett Ed., "Developments in Crystalline Polymers," Elsevier, London, Vol. 2, 1988, pp. 1–65; Lafferty et al., "Microbial Production of Poly-β-hydroxybutyric acid," H. J. Rehm and G. Reed, Eds., "Biotechnology", Verlagsgesellschaft, Weinheim, vol. 66, 1988, pp. 135–76; Müller and Seebach, *Angew. Chem. Int. Ed. Engl.* 32:477–502 (1993).

The key enzymes of PHA synthesis, the PHA synthases, have been studied in detail by many laboratories (Slater et al., 1988; Schubert et al., 1988; Peoples & Sinskey, 1989; Steinbüchel et al., 1992; Rehm & Steinbüchel, *Int. J. Biol. Macromol.* 25:3–19 (1999)) and can be genetically engineered into a diverse group of organisms including both other types of bacteria as well as plants.

Methods for producing PHAs in natural or genetically engineered organisms are described by Steinbüchel, A. "Polyhydroxyalkanoic Acids," in D. Byrom Ed., "Biomaterials", MacMillan Publishers, London, 1991, pp. 123–213; Williams and Peoples, *CHEMTECH*, 26:38–44, (1996); Steinbüchel and Wiese, *Appl. Microbiol. Biotechnol.*, 37:691–97 (1992); U.S. Pat. Nos. 5,245,023; 5,250,430; 5,480,794; 5,512,669; 5,534,432 to Peoples and Sinskey; Agostini, D. E. et al., *Polym. Sci.*, Part A-1, 9:2775–87 (1971); Gross, R. A. et al., *Macromolecules*, 21:2657–68 (1988); Dubois, P. I. et al., *Macromolecules*, 26:4407–12 (1993); Le Borgne, A. and Spassky, N., *Polymer*, 30:2312–19 (1989); Tanahashi, N. and Doi, Y., *Macromolecules*, 24:5732–33 (1991); Hori, Y. M. et al., *Macromolecules*, 26:4388–90 (1993); Kemnitzer, J. E. et al., *Macromolecules*, 26:1221–29 (1993); Hori, Y. M. et al., *Macromolecules*, 26:5533–34 (1993); Hocking, P. J. and Marchessault, R. H., *Polym. Bull.*, 30:163–70 (1993); Xie, W. et al., *Macromolecules*, 30:6997–98 (1997), and U.S. Pat. No. 5,563,239 to Hubbs, et al, the teachings of which are incorporated herein.

The PHAs disclosed herein can be prepared from a biological source such as microorganisms which naturally produce PHAs and which can be induced to produce the desired PHAs by manipulation of culture conditions and feedstocks. The PHAs disclosed herein can also be prepared from microorganisms genetically engineered as described herein, or higher organisms, such as plants, which have been genetically engineered to produce PHAs. The manipulation of culture conditions and feedstocks for the production of PHAs are well within the knowledge in the art. The PHAs may be purified by extraction with or precipitation from aqueous solutions, organic solvents, supercritical fluids, or combinations thereof.

Preparation of Thioester-containing PHAs

Thioester-containing PHAs can be prepared by feeding a sulfur-containing carbon source, a lone or in combination with another carbon source, to a variety of PHA accumulating bacteria or genetically engineered organisms. Exemplary genetically engineered organisms are for example bacteria such as E. coli, fungi, or plants. Exemplary substrates are thioalkanoic acid, alone or in combination with other carbon source or sources. In one embodiment, the thioalkanoic acid is a 3-thioalkanoic acid. Preferably, the thioalkanoic acid is 3-mercaptopropionate or 3,3'-Thiodipropionic acid (TDP).

For example, R. eutropha synthesizes a copolymer of 3-hydroxybutyrate and 3-mercaptopropionate, poly (3HB3–3MP), when 3-mercaptopropionic acid or 3,3'-thiodipropionic acid is provided as carbon source in addition to fructose or gluconic acid under nitrogen-limited growth conditions. The thioester linkages can be formed between the thiol groups of 3MP and the carboxyl groups of 3MP or 3HB, respectively. As another example, the R. eutropha strain H16 can use 3-hydroxybutyrate and use 3-mercaptopropionic acid to form a copolyester of 3HB and 3MP, poly(3HB-co-3MP). The structure of poly(3HB-co-3MP) is shown in FIG. 1.

Preparation of Thioether-containing PHAs

The preparation of thioether-containing PHAs is readily achieved by feeding a sulfur-containing carbon source, alone or in combination with another carbon source, to a variety of PHA accumulating bacteria or genetically engineered organisms. Exemplary genetically engineered organisms are for example bacteria such as E. coli, fungi, or plants. Preferably, the organism is a species of pseudomonades. Exemplary substrates are alkylthioalkanoic acids (ATAs) such as propylthioundecanoic acid (PTUD), propylthiooctanoic acid (PTO), octylthiohexanoic acid (OTHx), butylthiovaleric acid (BTV), or propylthiopropionic acid (PTP) as carbon source. For example, PTUD can be generated by growing P. putida KT2440 using PTUD as the sole carbon source. In another example, the metabolically engineered strain of the PHA negative mutant R. eutropha PHB-4 harboring plasmid pBBR1::phaC1 expressing the PHA$_{MCL}$ synthase from Pseudomonas mendocina can be used for forming thioether-containing PHAs.

The biosynthesis of thioether-containing PHAs can be carried out in various scales. For example, R. eutropha PHB$^-$4 harboring pBBR1::phaC1 can be cultivated at for example the 26 l-scale using for example a 30 l stirred tank bioreactor. After cultivation of a period such as 45 h, a large amount of the copolyester can be isolated.

4. Applications of PHAs

The thermoplastic and/or elastomeric features of PHAs allow various applications and uses in industry, e.g. in the packaging industry, medicine, pharmacy, agriculture or food industry with clear advantages of biodegradability and the origin from renewable resources (Hocking & Marchessault, 1994). Recently, polythioesters containing 3MP or other constituents and polyesters containing TDP have been chemically synthesized (Podkoscielny & Podgorski, 1996; Bandiera, et al. Eur. Pol. J. 33:1679–1683 (1997); Choi et al., J. Pol. Sci. 36:1189–1195 (1998); Kameyama et al., Macromol.32, 1407–1412 (1999). The sulfur-containing PHAs were reported to be properties which render the polymers suitable for preparing polymer electrolytes (Bandiera et al., 1997). Moreover, the sulfur-containing PHAs can have anti-bacterial, anti-viral, or anti-fungal properties.

The sulfur-containing PHAs allow various applications and uses in industry. Representative embodiments of the applications of the sulfur-containing PHAs include their uses in the packaging industry, medicine, pharmacy, agriculture or food industry.

In one preferred embodiment, the sulfur-containing PHAs can be used as an anti-bacterial agent, an anti-viral agent, or an anti-fungal agent. In one most preferred embodiment, the sulfur-containing PHAs can be used as anti-bacterial coatings.

In another preferred embodiment, the sulfur-containing PHAs are used as electrolytes.

The present invention will be further understood by reference to the following non-limiting examples.

EXAMPLES

General Experimental Procedures

GC/MS analysis. The polyester content was determined by methanolysis of 5–7 mg lyophilized cells in the presence of sulfuric acid, and the resulting methyl esters were characterized by gas chromatography (Brandl et al, Appl. Environ. Microbiol. 54:1977–1982 (1988)). For molecular analysis of the methyl esters, a coupled gas chromatography/mass spectrometry (GC/MS) was performed using a HP 6890 gas chromatograph equipped with a model 5973 mass selective detector (Hewlett Packard, Waldbronn, Germany). The obtained mass spectra were compared with the NIST '98 Mass Spectral Library with Windows Search Program Version 1.6, National Institute of Standards and Technology (U.S. Department of Commerce).

Elemental Sulfur Analysis. Sulfur analysis was performed by the Mikroanalytisches Labor Beller (Gottingen, Germany) according to the method of Grote and Krekeler (DIN 51768).

Molecular mass analysis. The molecular masses of purified polyesters were estimated by gel-permeation chromatography (GPC) relative to polystyrene standards. Analysis was performed on four Styragel columns (HR 3, HR 4, HR 5, HR 6) connected in line in a Waters GPC apparatus (Waters, Milford, USA). Samples were eluted with chloroform at a flow rate of 1.0 ml/min and at 35° C., and the eluted compounds were monitored by a Waters 410 differential refractometer. Polydispersity and the number average ($M_N$) and weight average ($M_W$) molar masses were calculated by using the Millenium Chromatography Manager GPC software (Waters, Milford, USA).

Infrared spectroscopic analysis. The IR-spectra were taken with a fourier transform spectrometer IFS 28 (Bruker, Bremen/Karlsruhe, Germany). The samples were dissolved in $CHCl_3$ and deposited as a film on a sodium chloride disk. Alternatively, a liquid cell with sodium chloride windows (path length 0.5 mm) was used with a chloroform solution of the polymer (2 mg sample/ml).

Nuclear magnetic resonance spectroscopic analysis. All NMR experiments were performed on a Varian Unity Plus 600 spectrometer ($^1H$: 599.14 MHz, $^{13}C$: 150.66 MHz). The $^1H$ and $^{13}C$ assignments were confirmed through gCOSY (gradient $^1H,^1H$-COSY), 1D TOCSY ($^1H$ total correlation spectroscopy with selective excitation), gHSQC ($^1H$, $^{13}C$ gradient heteronuclear single quantum coherence) and gHMBC ($^1H$, $^{13}C$ gradient heteronuclear multiple bond correlation) spectra.

Example 1

Bacterial Synthesis of a Sulfur Containing Polymer with Thioester Linkages

This example describes the bacterial production of a copolyester consisting of 3-hydroxybutyrate and 3-mercaptopropionate, poly(3HB-co-3MP). The incorporation of 3MP is catalyzed by an enzymatic reaction resulting in a thioester bond.

Methods

Bacterial strains and culture conditions. R. eutropha H16 (DSM 428) and R. eutropha PHB$^-$4 (DSM 541) were cultivated in nutrient broth (NB) growth medium or in mineral salts medium (MSM) (Schlegel et al., (1961) Arch. Mikrobiol. 38, 209–222) at 30° C. in Erlenmeyer flasks under aerobic conditions on a rotary shaker with 130 strokes/min. In order to promote PHA accumulation, the ammonia concentration was reduced to 0.05% (w/v). Carbon sources were added from filter-sterilized 20% (w/v) stock solutions at the concentrations indicated in the text.

Fed-batch cultivation of R. eutropha H16 at a 26-l scale was done in a stirred (at 200–400 rpm) and aerated (15–20

1 min$^{-1}$) 30-l stainless-steel fermenter (Biostat UD30, B. Braun, Biotech International, Melsungen, Germany). Fermentations were carried out in MSM, and the pH was adjusted to 7.0.

Polymer isolation from lyophilized cells. Poly(3HB) and poly(3HB-co-3MP) were extracted from lyophilized cells with chloroform, filtered, precipitated in 10 volumes of ethanol, and dried under a constant air stream. In order to obtain highly purified polymer, the precipitation procedure was repeated at least threefold.

Infrared spectroscopic analysis. Infrared spectrum of poly (3HB-co-3MP)v(cm$^{-1}$); film on NaCl disk. 2983 m (CH, CH2,CH3); 2933 m (CH,CH2,CH3); 1737 s (ester C=O valence); 1688 (thioester C=O valence); 1380 m; 1302 m; 1260 m (CH2-S); 1185 s (ester C—O); 1134 m; 1101 m; 1057 s; 978 m; 760 w; 700 w.

Nuclear magnetic resonance spectroscopic analysis. The measurements were carried out at 298 K with a sample of 10 mg of the isolated polymer dissolved in 1 ml CDCl$_3$. While the three investigated polymer samples (see Table 3) showed very close values for the sets of chemical shifts, there were some variations regarding the amount of incorporated 3MP. Therefore, in the following the NMR spectroscopic results of one representative polymer originating from the 50 h fed batch fermentation of R. eutropha (Table 3) are listed in the order of determined sequence types.

-3HB-3HB-: δ ($^1$H) 5.23 (m, 1H, 3-H), 2.58 (dd, $^2$J=15.5 Hz, $^3$J$_{2,3}$=7.3 Hz 1H, 2-H), 2.45 (dd, $^2$J=15.5 Hz, $^3$J$_{2,3}$=6 Hz, 1H, 2-H'), 1.25 (d, $^3$J$_{3,4}$=6.3 Hz, 3H, 4-H); δ ($^{13}$C) 169.1 (C$_q$, C-1, ester), 67.6 (CH, C-3), 40.8 (CH$_2$, C-2), 19.7 (CH$_3$, C-4); gHMBC: 2.58/169.1, 2.45/169.1, 5.23/169.1.

-3MP-3MP-: δ ($^1$H) 3.13 (m, $^3$J=7 Hz, 2H, 3-H), 2.84 (m, $^3$J=7 Hz, 2H, 2-H); δ ($^{13}$C) 196.7 (Cq, C-1, thioester), 43.3 (CH$_2$, C-2), 24.0 (CH$_2$, C-3); gHMBC: 2.84/196.7, 3.13/196.7.

-3HB-3MP-: δ ($^1$H) 5.27 (m, 1H, 3-H), 2.86 (m, 1H, 2-H), 2.70 (m, 1H, 2-H'), 1.27 (d, 3H, 4-H); δ ($^{13}$C) 195.2 (Cq, C-1, thioester), 67.8 (CH, C-3), 49.4 (CH$_2$, C-2), 19.8 (CH$_3$, C-4); GHMBC: 2.86/195.2, 2.70/195.2, 5.27/195.2.

-3MP-3HB-: δ ($^1$H) 3.10 (m, 2H, 3-H), 2.58 (m, 2H, 2-H); δ ($^{13}$C) 170.5 (C$_q$, C-1, ester), 34.4 (CH$_2$, C-2), 24.0 (CH$_2$, C-3); gHMBC: 2.58/170.5, 3.10/170.5.

-3HP-3HB-: δ ($^1$H) 4.30 (m, 2H, 3-H), 2.59 (m, 2H, 2-H); δ ($^{13}$C) 60.0 (CH$_2$, C-3), 33.9 (CH$_2$, C-2); gHMBC: 4.30/169.8.

-3HP-3MP-: δ ($^1$H) 4.35 (m, 2H, 3-H), 2.88 (m, 2H, 2-H); δ ($^{13}$C) 195.8 (C$_q$, C-1, thioester), 60.0 (CH$_2$, C-3), 43.7 (CH$_2$, C-2); gHMBC: 2.88/195.8, 4.35/195.8, 4.35/171.3.

Results and Discussion

Studies on growth and polymer accumulation by R. eutropha. The Gram-negative polyhydroxyalkanoate-(PHA-) accumulating bacterium R. eutropha synthesized a copolymer of 3-hydroxybutyrate and 3-mercaptopropionate, poly(3HB3-3MP), when 3-mercaptopropionic acid or 3,3'-thiodipropionic acid was provided as carbon source in addition to fructose or gluconic acid under nitrogen-limited growth conditions. The peculiarity of this polymer was the occurrence of thioester linkages derived from the thiol groups of 3MP and the carboxyl groups of 3MP or 3HB, respectively, which occurred besides the common oxoester bonds of PHAs. Depending on the cultivation conditions and the feeding regime, poly(3HB-co-3MP) contributed up to 19% of the cellular dry weight, with a molar fraction of 3MP of up to 43%. The chemical structure of poly(3HB-co-3MP) was confirmed by gas chromatography/mass spectrometry, infrared spectroscopy, $^1$H- and $^{13}$C-nuclear magnetic resonance spectroscopy, and elemental sulfur analysis.

Although R. eutropha strain H16 is not able to use 3-mercaptopropionic acid or 3,3'-thiodipropionic acid (TDP) as sole carbon sources for growth, a copolyester of 3HB and 3MP, poly(3HB-co-3MP) (FIG. 1), was synthesized when these substances were provided in addition to fructose or gluconic acid under nitrogen limitation. The PHB-negative mutant PHB-4 of strain H16 did not synthesize a polymer containing 3MP.

TABLE 3

Characterization of poly(3Hb-co-3MP) obtained from different fermentation of R. eutropha*

| Cultivation conditions: Type and duration of fermentation and media additives | A | B | C | D |
| --- | --- | --- | --- | --- |
| Batch culture, 96 h 0.05% NH$_4$Cl, 0.2% fructose, 0.2% TDP | 19.2% | 9.96% | 26.9 mol % | 490.000 |
| Fed batch culture, 50 h 0.01% NH$_4$Cl, 0.4% gluconic acid, 0.2% TDP, each 0.2% TDP were additionally added after 9 h, 15 h and 32 h | 9.2 | 12.88 | 34.9 | 1,120.000 |
| Batch culture, 96 h 0.05% NH$_4$Cl, 0.3% gluconic acid, 0.1% 3 MP | 11.4 | 15.67 | 42.5 | 790.000 |

*R. eutropha strain H16 was cultivated at 30 C in MSM. The polymer yield referring to the cellular dry weight was determined by gas chromatography (Brandl et al., 1988). The element sulfur was analyzed by the method of Groteand Kerkeler (DIN 51768), and the derived molar fraction of 3MP was calculated. The weight-average molecular weight were estimated by gel-permeation chromatography (GPC relative to polystyrene standards. Abbreviations: 3MP, 3-mercaptopropionic acid; TDP, 3,3'-thiodipropionic acid; CDW, cellular dry weight; M$_w$, weight-average molecular weight.
A: polymer content [w/w, of CDW]; B: sulfur content of the polymer; C: 3MP content of the polymer; D: weight average molecular weight of the polymer [g/mol].

Table 3 summarizes the culture conditions, sulfur contents, polymer yields, molar fractions of 3MP, and the molecular masses of three different batches of the polymer. Depending on the culture conditions, the polymer content of the cells varied from 9.2 to 19.2% (w/w). Usually, R. eutropha accumulates poly(3HB) when the provided carbon source is directly metabolized to acetyl-CoA, and under certain conditions the polymer content can contribute up to 96% of the cellular dry weight (Pedrós-Alio et al., (1985) Arch. Microbiol. 143, 178–184). In this study, a decrease of total poly(3HB-co-3MP) content was observed simultaneously with an increase in the molar 3MP fraction when the utilizable carbon source was restricted. Thus, a molar fraction of 3MP of 42.5 mol% was obtained during batch cultivation of R. eutropha with nitrogen- and gluconic acid limitation in the presence of 0.1% (w/v) 3-mercaptopropionic acid.

Growth experiments employing mineral salts medium containing 3-mercaptopropionic acid or TDP plus a carbon source that is readily utilized such as gluconic acid, revealed that 3-mercaptopropionic acid at concentrations higher than 0.1% (w/v) in the medium impaired the growth of R. eutropha and other bacteria. In contrast to 3-mercaptopropionic acid, TDP did not exert any toxic effects on the growth of R. eutropha up to concentrations of 1.5% (w/v).

Chemical analysis of poly(3HB-co-3MP). Gas chromatographic (GC) analyses of cells from R. eutropha cultivated with 3-mercaptopropionic acid and TDP in addition to fructose or gluconic acid under conditions promoting PHA accumulation, showed peaks with a retention time of $R_T$=8.88 min, in addition to the 3HB-methylester at a $R_T$ of 9.55 min. Consequently, the polymer was isolated from the cells and highly purified. All subsequent analyses were performed with the purified polyester. Three batches of purified polymer obtained from three different fermentations (Table 3) were analyzed. The peaks were analyzed by mass spectrometry (MS), and the 3MP-methylester was identified by the isotope pattern. Comparison with the NIST-data base confirmed the identification of the 3MP-methylester as an acid methanolysis product of poly(3HB-co-3MP).

In order to determine the precise molar fraction of 3MP in the polymer, elemental sulfur analysis of the isolated and purified poly(3HB-co-3MP) was carried out. The total sulfur content varied from 9.96 to 15.67% (w/w), thus the calculated 3MP content varied from 26.9 to 42.5 mol% in the three polymer batches.

Molecular weight analyses of poly(3HB-co-3MP). The molecular weights of the isolated polymers were determined by gel-permeation chromatography (GPC) relative to polystyrene standards. The weight average molar masses ($M_W$) of poly(3HB-co-3MP) varied from 0.49 to $1.15 \times 10^6$ g/mol with polydispersity indices ($M_W/M_N$) ranging from 4.2 to 7.0. Compared with the homopolyester poly(3HB) synthesized by R. eutropha from gluconic acid under conditions permissive for PHA accumulation, the molecular weights of poly(3HB-co-3MP) correlated with those of poly(3HB) reported by Rehm & Steinbüchel (Rehm & Steinbüchel, Int. J Biol. Macromol. 25:3–19 (1999)).

Infrared spectroscopic analysis of poly(3HB-co-3MP). The IR-spectrum reflects both monomeric units. All absorptions due to the PHB moiety appeared in the spectrum, and in addition a strong absorption band at 1688 $cm^{-1}$ was detected as it is expected for the C=O valence vibration of a thioester bond (Colthup et al., 1964). The intensity of this band was proportional to the sulfur content, which was determined by elemental analysis.

The IR spectroscopic analysis gave further insights into the chemical structure without hydrolysis of the polymer. Poly(3HB-co-3MP) is the first example of a polymer in which the linkage between the constituents is modified: the -3HB-3MP- and -3MP-3MP- are linked by thioester bonds that occur in addition to the oxoester linkages of-3MP-3HB- and -3HB-3HB-.

Nuclear magnetic resonance spectroscopic analysis of poly(3HB-co-3MP). The 600 MHz $^1$H NMR spectrum of a typical poly(3HB-co-3MP) sample was analyzed. The fraction of 3MP present in the polymer was determined by integration of the 3-H signals of 3HB and 3MP resonating at δ 5.23 and 3.23, respectively. The calculated incorporation rate of 34% is in good agreement with the 34.9% determined by elemental sulfur analysis for this polymer sample (Table 3). In addition, traces of 3-hydroxypropionic acid (3HP) resonating at δ 4.30 were detected (see below).

In principle, there are four possibilities of combining the monomers. The homopolymer regions of 3HB and 3MP offer a relatively homogeneous environment. Accordingly, such sequences lead to sharp and intense signals in the $^1$H- and $^{13}$C-NMR spectra. The observed chemical shifts in the homopolymer regions of 3HB are in good agreement with the signal assignment of poly(3HB-co-3HP), while the assignment of the homopolymer region of 3MP was done in comparison with the methylester of 3MP.

In addition to these two types of linkages, the signals of -3HB-3MP- and -3MP-3HB- containing thioester and ester bonds, respectively, can also be expected in the isolated polymer. These linkages can be traced by $^1$H, $^{13}$C long-range correlation spectra. The gHMBC-spectrum showed correlation signals between the protons of 3HB and the C-1 of the thioester, and of 3MP and C-1 of the ester. Compared with the signals of the homopolymer regions of 3HB and 3MP, these signals were of lower intensity. Because of signal overlap the exact molar relation between the homo- and the copolymer regions could not be determined. However, definitive signal assignment could be achieved through 1D TOCSY experiments by selective excitation at various resonance frequencies. In addition to these four main chain sequences, indications for the presence of small amounts of -3HP-3HB- and -3HP-3MP- were found. Although traces of 3HP were detected by NMR spectroscopic analyses, GC/MS analyses did not reveal any occurrence of 3HP or other constituents in the purified polymers.

TDP should be cleaved into 3MP and 3HP (FIG. 3), because 3MP amounted up to 34.9 mol % of the constituents of the polymer obtained during fed batch cultivation of R. eutropha with nitrogen- and gluconic acid limitation in the presence of an excess of TDP. 3MP and 3HP are subsequently converted to the corresponding CoA thioesters. 3HP was identified previously as a constituent of PHAs synthesized by R. eutropha (Nakamura et al., Macromol. Rep. A28, 15–24 (1991)).

Figure 4:
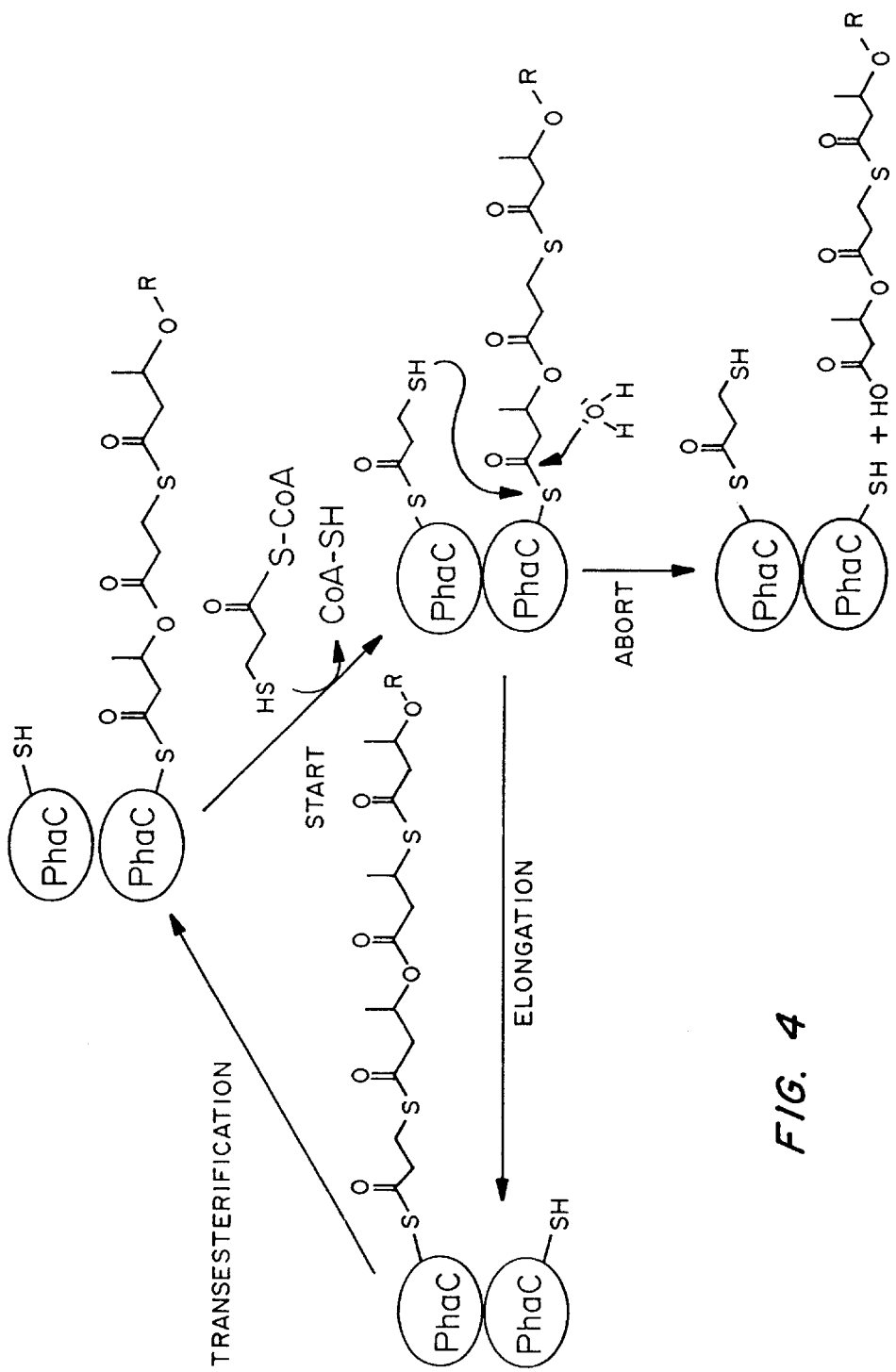
FIG. 4 is a schematic of the putative catalytic cycle of the PHA synthase (PhaC) for the incorporation of 3MP into poly(3HB-co-3MP) in *R. eutropha*.

3MP-CoA can be used as substrate by the PHA synthase. Surprisingly, the PHA synthase is able to catalyze the formation of both oxoester and thioester bonds. The PHB-negative mutant R. eutropha PHB-4 was incapable of synthesizing poly(3HB-co-3MP), confirming the involvement of PHA synthase. The proposed catalytic mechanism of the PHA synthase in R. eutropha involves two thiol groups which derive from two cystein residues of the enzyme subunits (PhaC) forming a homodimer (Müh et al., 1999; Rehm & Steinbüchel, 1999) (FIG. 4). These thiol groups covalently bind the growing polyester chain, and the constituent that then will be incorporated during the next turn of the cycle. A nucleophilic attack of the free electron pair of the hydroxy group of the latter at the carbonyl carbon atom of the nascent polymer is suggested. The sulfhydryl group of 3MP is also providing a free electron pair for this nucleophilic attack, and 3MP is incorporated resulting in the formation of a thioester (FIG. 4).

Though rather little is known about the degradation of the sulfur-containing substances TDP and 3-mercaptopropionic acid, a biological conversion into intermediates of central pathways is very likely to occur because 3-mercaptopropionic acid is not a xenobiotic and is occurring naturally.

Example 2

Synthesis and Analysis of Poly(3HB-co-3MB)

Methods and Materials

Bacterial strains and culture conditions. R. eutropha H16 (DSM 428) and R. eutropha PHB-4 (DSM 541) were cultivated in nutrient broth (NB) growth medium or in mineral salts medium (MSM) (Schlegel, 1961, supra) at 30° C. in Erlenmeyer flasks under aerobic conditions on a rotary shaker with 130 strokes/min. In order to promote PHA accumulation, the ammonia concentration was reduced to 0.05% (w/v). Carbon sources were added from filter-sterilized stock solutions at the concentrations indicated in the text.

Synthesis of 3-mercaptobutyric acid. According to Schjanberg (1941) 3-mercaptobutyric acid was synthesized from crotonic acid and thioacetic acid via 3-acetylmercaptobutyric acid (FIG. 1) by dissolving 86 g crotonic acid in 500 ml H$_2$O and adding 76 ml thioacetic acid. The reaction mixture was stirred for 24 h at 25° C. and subsequently 6 h at 50° C. For alkaline hydrolysis, the obtained 3-acetylmercaptobutyric acid was treated with 50% (v/v) NaOH for 24 h. Finally, the pH was adjusted to 7.0. The concentration of the obtained 3-mercaptobutyric acid stock solution, which also contained equimolar amounts of acetic acid, was assumed to be 1.4 M, although an exact quantification was not possible, yet. The successful synthesis of 3-mercaptobutyric acid was confirmed by GC/MS.

Polymer isolation from lyophilized cells. Poly(3HB) and poly(3HB-co-3MB) were extracted from lyophilized cells with chloroform, filtered, precipitated in 10 volumes of ethanol, and dried under a constant stream of air. In order to obtain highly purified polymer samples, the precipitation procedure was repeated at least threefold.

Infrared spectroscopic analysis. Infrared spectrum of poly (3HB-co-3MB)ν(cm$^{-1}$); film on NaCl disk. 2983 m (CH, CH2,CH3); 2933 m (CH,CH2,CH3); 1724 s (ester C=O valence); 1687 (thioester C=O valence); 1380 m; 1302 m; 1260 m(CH2-S); 1185 s(esterC-O); 1134m; 1101 m; 1057 s; 978 m; 760 w; 700 w.

Results

Figure 5:
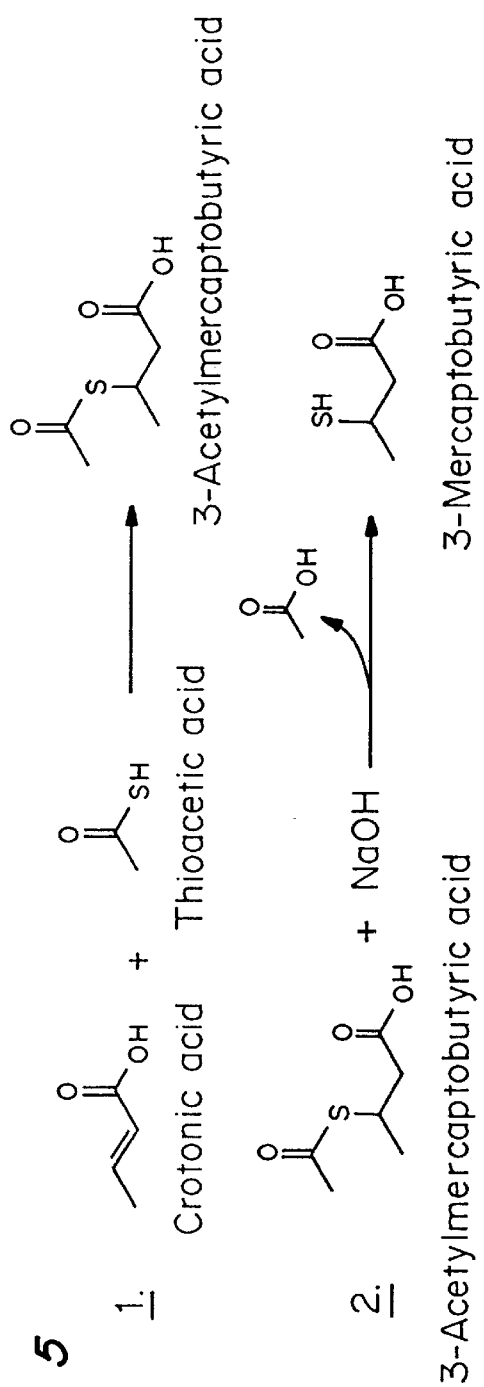
FIG. 5 is a schematic of the chemical synthesis of 3-mercaptobutyric acid.

Synthesis of poly(3HB-co-3MB) by R. eutropha. In this study, 3-mercaptobutyric acid (FIG. 5) was synthesized and used this substance as substrate for cultivation experiments with R. eutropha under conditions promoting PHA accumulation. R. eutropha was not able to use 3-mercaptobutyric acid as sole carbon source for growth; thus, gluconate was provided as an utilizable carbon source. Cells of R. eutropha strain H16 were cultivated in mineral salts medium in the presence of 0.2% (w/v) gluconate plus 50 mM 3-mercaptobutyric acid and analyzed gas chromatographically (GC). The total polymer yield contributed up to 31% of the cellular dry weight. The GC pattern of the isolated polymer revealed besides the 3HB methyl ester peak with a retention time of R$_T$=9.41 min, an additional peak with a retention time of R$_T$=8.29 min. The peaks were analyzed by mass spectrometry (MS), and the 3MB methyl ester was clearly indicated by the isotope pattern.

Characterization of poly(3HB-co-3MB). The occurrence of sulfur in this polymer was further confirmed by elemental analysis. The total sulfur content of the polymer amounted 11.65% (w/w), thus the molar fraction of 3MB was calculated as 33.24 mol %.

Figure 2:
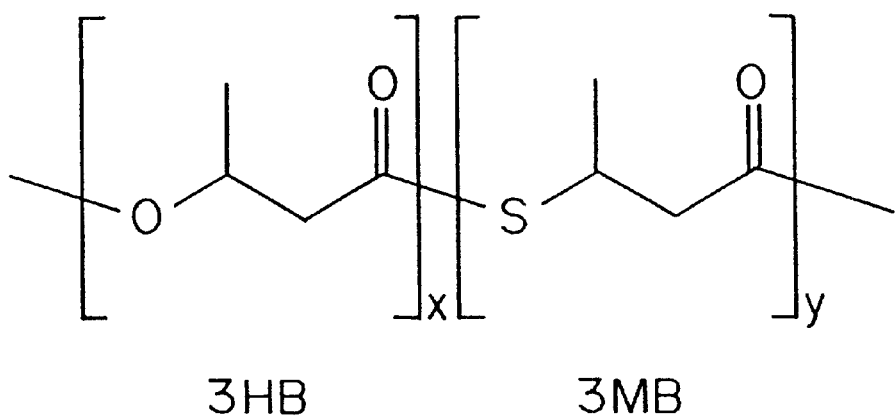
FIG. 2 is the structural formula of poly(3HB-co-3MB).

According to the results of the performed analyses, and in consideration of the provided substrate, a copolymer was detected: poly(3HB-co-3MB) (FIG. 2). The main features of poly(3HB-co-3MB) are summarized in Table 2.

TABLE 2

Characterization of poly(3Hb-co-3MB) synthesized by R. eutropha*

| Provided carbon sources | A | B | C | D | E |
|---|---|---|---|---|---|
| 0.2% (w/v) sodium gluconate plus 50 mM 3-Mercaptobutyrate acid | 31.3% | 11.65% | 33.2 mol % | 790.000 | 2.05 |

*R. eutropha strain H16 was cultivated for 48 h at 30 C in MSM (Schlegel et al., 1961. The polymer yield referring to the cellular dry weight was determined by gas chromatography (Brandl et al., 1988). The element sulfur was analyzed by the method of Groteand Kerkeler (DIN 51768), and the derived molar fraction of 3MB was calculated. The weight-average molecular weight and polydispersity ($M_w/M_N$) of the polymer were estimated by gel-permeation chromatography (GPC relative to polystyrene standards. Abbreviations: 3MB, 3-mercaptobutyrate; CDW cellular dry weight; $M_w$ weight-average molecular weight; $M_N$, number-average molecular weight.
A: polymer content [w/w, of CDW]; B: sulfur content of the polymer; C: 3MB content of the polymer; D: weight average molecular weight of the polymer [g/mol]; E polydispersity of ($M_w/M_N$) the polymer.

The supposed thioester linkages between the thiol groups of 3MB and the carboxyl groups of 3HB or 3MB, respectively, were proven by infrared (IR) spectroscopy. The obtained IR spectrum revealed in comparison to the spectrum of poly(3HB) an absorption band at 1687 cm$^{-1}$, as it is expected for the carbonyl vibration of a thioester bond (Colthup et al., (1964) Introduction to Infrared and Raman Spectroscopy. Academic Press NY, London).

The chemical structure of poly(3HB-co-3MB) was also analyzed by nuclear magnetic resonance spectroscopy confirming the suggested structure of the polymer as shown in FIG. 2.

Example 3

Synthesis of Poly(3-Hydroxy-S-propyl-ω-thioalkanoates)

Materials and Methods

Bacterial strains and culture conditions. The PHA-negative mutant R. eutropha PHB$^-$4 (DSM 541) and a recombinant strain of R. eutropha PHB$^-$4 harbouring plasmid pBBR1::phaC1 expressing the PHA synthase 1 of Pseudomonas mendocina, as well as Pseudomonas putida KT2440 (Worsey & Williams, "Metabolism of toluene and xylenes by Pseudomonas putida (arvilla) mt-2: evidence for a new function of the TOL plasmid" in J Bacteriol 124:7–13 (1975)), P. aeruginosa PAO1 (ATCC 15692), P. oleovorans (ATCC 29347), and P. mendocina (DSM 50017) were used. Cultivations were performed in nutrient broth (NB) medium or mineral salts medium (MSM) according to Schlegel (1961), supra, to which different alkylthioalkanoic acids were added as carbon sources from filter-sterilized 10% (w/v) stock solutions at the concentrations indicated in the text. Fed batch cultivations were carried out under aerobic conditions at 30° C. in 2 l Erlenmeyer flasks containing 500 ml of medium which were agitated at 130 r.p.m. In order to promote PHA accumulation, the ammonia concentration was reduced to 0.05% (w/v) in MSM.

Fed-batch cultivation of *R. eutropha* PHB-4 harboring plasmid pBBR1::phaC1 was done on a 26–1 scale in a stirred (at 50–400 r.p.m) and aerated (15–20 l×min$^{-1}$) 30 l stainless-steel fermenter (Biostat UD30, B. Braun, Biotech International). The fermentation was carried out in MSM. The temperature and the pH were automatically controlled at 30° C. and 7.0, respectively; the airflow rate and the stirring speed were 1.0 vvm and 400 r.p.m, respectively. Cell growth was monitored spectrometrically at 600 and 850 nm. The MSM contained 1.0% (w/v) sodium gluconate and 300 mg/l kanamycine from the beginning. Sodium gluconate and ammonium chloride were fed additionally according to the respective growth parameters. Propylthiooctanoic acid was added at the end of the exponential growth phase successively in portions of each 0.05% (w/v) from a filter sterilized stock solution to a final concentration of 0.8% (w/v). At the end of the cultivation experiment, the cells were harvested by centrifugation and lyophilized.

Chemical synthesis of alkylthioalkanoic acids. Propylthioundecanoic acid (PTUD), propylthiooctanoic acid (PTO), propylthiohexanoic acid (PTHx), propylthiobutyric acid (PTB), propylthiopropionic acid (PTP), butylthiovaleric acid (BTV), and octylthiohexanoic acid (OTHx) were chemically synthesized as described previously from alkylthiol and ω-bromoalkanoic acids (Skrede et al, "Thia fatty acids, metabolism and metabolic effects" in *Biochim Biophys Acta* 1344:115–31 (1997)). Propanethiol, butanethiol, octanethiol, 11-bromoundecanoic acid, 8-bromooctanoic acid, 6-bromohexanoic acid, 5-bromovaleric acid, 4-bromobutyric acid, and 3-bromopropionic acid were purchased from Sigma chemical company (Deisenhofen, Germany).

Isolation of PHAS. PHAs were extracted from lyophilized cells with hot chloroform using a Soxhlet apparatus. The extracted crude PHAs were precipitated in 10 volumes of cold methanol. In order to obtain highly purified polymer samples for chemical analyses, the precipitation from a solution in chloroform was repeated at least four times. The purified polymer was finally dried under a constant air stream.

Partial pyrolysis of polymers. Identification of the constituents of PHAs was also performed by partial pyrolysis. For this, 5 mg of isolated polymer were transferred to the bottom of a small glass tube, which was flushed with argon and subsequently evacuated to 1 mbar. The lower part of the tube was then heated to approximately 500° C. until the polymer was completely degraded. Decomposition products condensed in the upper part of the glass tube. After adjusting the temperature to room temperature, the products were dissolved in 2 ml methanol/chloroform (1/1). A part of this solution was used as it was for ESI-MS, the other was esterified for GC/MS with TMSD.

ESI-MS and ESI-MS/MS analysis. This soft ionization method was used to characterize the oligomers formed by pyrolysis of the polymers. All measurements were done on a Quattro LCZ (Micromass) with nanospray inlet.

Infrared spectroscopic analysis. Infrared spectrum of poly (3HPTA) v (cm$^{-1}$); film on NaCl disk: 2983 m(medium) (CH,CH2,CH3); 2933 m (CH,CH2,CH3); 1741 s(strong) (ester C=O valence); 1380 m; 1302 m; 1185 s (ester C-O); 1134 m; 1101 m; 1057 s; 978 m; 760 w(weak); 700 w.

Results

Growth and PHA accumulation of bacteria on alkylthioalkanoic acids. To evaluate the capabilities of various pseudomonades to use alkylthioalkanoic acids (ATAs) as carbon and energy sources for the synthesis of sulfur containing PHAs, growth experiments were carried out employing MSM agar plates which contained propylthioundecanoic acid (PTUD), propylthiooctanoic acid (PTO), octylthiohexanoic acid (OTHx), butylthiovaleric acid (BTV), or propylthiopropionic acid (PTP) as carbon sources. Table 4 summarizes the results, revealing that all Pseudomonas strains investigated in this study were able to use PTUD, PTO, OTHx and BTV as sole carbon sources.

TABLE 4

Growth of different Pseudomonas species on MSM agar plates containing different ATAs as sole carbon sources.

| | Carbon source | | | | |
|---|---|---|---|---|---|
| | A | B | C | D | E |
| *P. putida* | +* | + | ++ | +* | − |
| *P. mendocina* | ++* | ++ | ++ | +* | − |
| *P. aeruginosa* | ++* | + | ++ | +* | − |
| *P. oleovorans* | ++* | + | ++ | +* | − |

+, growth; ++, good growth; −, no growth; *, thiol odor detected.
Abbreviations: PTUD, propylthioundecanoic acid; PTO, propylthiooctanoic acid; OTHx, octylthiohexanoic acid; BTV, butylthiovaleric acid; PTP, propylthiopropionic acid.
Conditions: A, 0.4% (w/v) PTUD; B, 0.4% (w/v) PTO; C, 0.6% (w/v) OTHx; D, 0.3% (w/v) BTV; 0.2% (w/v) PTP.

Good growth occurred with PTUD and OTHx at concentrations up to 1% (w/v) in the medium, whereas PTO and BTV impaired cell growth if provided at concentrations higher than 0.8% or 0.4% (w/v), respectively. Moreover, a characteristic thiol smell was detected during cultivation of the bacteria on PTUD or BTV, respectively. In contrast, PTP was not used by any bacterium for growth.

GC analyses of cells of *P. mendocina*, *P. aeruginosa*, and *P. oleovorans* did not provide evidence that the cells had synthesized PHAs containing unusual constituents after cultivation in the presence of ATAs, including the addition of various cosubstrates. The PHA$_{MCL}$ accumulated by these bacteria consisted mainly of 3-hydroxyhexanoate (3HHx), 3-hydroxyheptanoate (3HHp), 3-hydroxyoctanoate (3HO), 3-hydroxynonanoate (3HN), 3-hydroxydecanoate (3HD), and 3-hydroxydodecanoate (3HDD) depending on the cultivation conditions.

PHA accumulation of *P. putida* KT2440 in the presence of PTUD.

The growth of *P. putida* KT2440 was significantly lower in comparison to other pseudomonades when PTUD was provided as sole carbon source (Table 4). *P. putida* KT2440 was the only Pseudomonas species investigated in this study. GC analysis revealed an unusual composition of PHAs after cultivation in MSM containing 0.35% (w/v) PTUD and equimolar amounts of nonanoic acid (v/v). An elemental sulfur analysis was done for the isolated polymer. It revealed a content of 6.02% (w/w) sulfur. Besides 3HHp, 3HN, and small amounts of 3HO, 3HD, 3HUD, and 3HDD, respectively, a significant amount of different sulfur containing constituents were detected by gas chromatography.

Biosynthesis of poly(3-hydroxypropylthioalkanoate), poly(3HPTA), by a recombinant strain of *R. eutropha*. The metabolically engineered strain of the PHA negative mutant *R. eutropha* PHB-4 harboring plasmid pBBR1::phaC1 expressing the PHA$_{MCL}$ synthase from *Pseudomonas mendocina* was used for further growth and PHA accumulation studies. ATAs were used as carbon sources.

Since growth of *R. eutropha* PHB-4 harboring pBBR1::phaC1 in MSM containing PTO as the sole carbon source was very poor, cultivations were carried out in complex medium (NB) or in MSM containing sodium gluconate as second utilizable carbon source in addition to PTO. In the presence of PTO in the medium, R. eutropha PHB-4 pBBR1::phaC1 synthesized a hitherto unknown polyester revealing exclusively 3-hydroxypropylthiobutyrate, 3-hydroxypropylthiohexanoate, and 3-hydroxypropylthiooctanoate as polymer constituents, poly (3HPTB-co-3HPTHx-co-3HPTO). The cultivation conditions, PHA contents of the cells, sulfur contents of the polymers as well as the molecular masses and polydispersity indices of the isolated poly(3HPTA)s obtained from four different batches, are shown in Table 5.

In order to test whether larger amounts of poly(3HPTB-co-3HPTHx-co-3HPTO) can be produced biotechnologically, and to obtain sufficient amounts for detailed analysis, R. eutropha PHB-4 harboring pBBR1::phaC1 was cultivated at the 26 l-scale using a 30 l stirred tank bioreactor. After 45 h cultivation, 190 g cellular dry mass was obtained from which 45 g of the copolyester were isolated.

TABLE 5

Characterization of poly(3HPTO-co-3HPTHx-co-3HPTB) obtained from different cultures of R. eutropha PHB 4 harboring pBBR1::phaC1*

| Cultivation conditions | A | B | C | D |
|---|---|---|---|---|
| Batch culture, 72 h NB + 0.15% (w/v) PTO | 43 | 16.80 | 105,819 | 2.3 |
| Batch culture, 72 h NB + 0.55% (w/v) PTO | 43 | 17.48 | 110,677 | 2.5 |
| Batch culture, 72 h MSM + 1% (w/v) sodium gluconate + 0.55% (w/v) PTO | 34 | 16.62 | 135,000 | 2.1 |
| Fed batch culture, 45 h MSM + 1% (w/v) sodium gluconate + 16 × 0.05% (overall 0.8%, w/v) PTO | 24 | 14.52 | 102,604 | 2.4 |

*Cultivations were done at 30° C. in 21 Erlenmeyer flasks or in a bioreactor as described in the text. The polymer yield referring to the cellular dry weight was determined gravimetrically. The elemental sulfur content was analyzed by the method of Grote and Kerkeler (DIN 51768). The molecular weight ($M_w$) and polydispersity ($M_w/M_N$) of the polymers were estimated by gel permeation chromatography (GPC) relative to polystyrene standards.
Abbreviations: NB, nutrient broth; MSM mineral salts medium; CDW, cellular dry weight; PTO, propylthiooctanoic acid.

TABLE 5-continued

Characterization of poly(3HPTO-co-3HPTHx-co-3HPTB) obtained from different cultures of R. eutropha PHB 4 harboring pBBR1::phaC1*

| Cultivation conditions | A | B | C | D |
|---|---|---|---|---|

A: polymer content [w/w, of CDW]; B: sulfur content of the polymer; C: 3MB content of the polymer; D: weight average molecular weight of the polymer [g/mol]; E polydispersity of ($M_w/M_N$) the polymer.

Chemical analysis of poly(3HPTB-co-3HPTHx-co-3HPTO). Infrared (IR) spectroscopic analysis of the purified polymer samples revealed a strong absorption band at 1741 $cm^{-1}$, as it is expected for the carbonyl vibration of an ester bond, indicating polymerized constituents with carboxyl and hydroxyl functional groups. The presence of a thioether group cannot be clearly deduced from the IR spectrum, because the $CH_2S$-frequency is hidden in the complex fingerprint region.

Polymer samples were also analyzed by nuclear magnetic resonance (NMR) spectroscopy, indicating propyl residues.

After pyrolysis of the polymer and subsequent methylation of the pyrolysis mixture with TMSD, three different monomeric S-propyl-ω-thioalkenoic acids were identified by GC/MS. The double bond was formed by the elimination of the adjacent fatty acid within the decomposition process.

The mass spectra were in good agreement with the expected structures. All spectra showed the loss of a methoxy radical and/or methanol indicating the presence of an ester group, and loss of propanethial and/or propylthio radical corresponding to the thiopropyl substituent. Furthermore, the presence of sulfur was clearly indicated by the characteristic isotope pattern.

Negative ion ESI/MS showed groups of oligomers formed by combinations of 3HPTB, 3HPTHx, and 3HPTO. ESI/MS/MS of the pseudomolecular ions suggested that the monomers were randomly combined (Table 6). The fragmentation of the trimer m/z 535 is given as an example. The loss of the three possible monomers (as their corresponding olefins) with similar intensities gave proof that the trimer was a mixture of isomers with 3HPTB-, 3HPTHx-, and 3HPTO-terminations. Mass spectrometric analyses of oligomers (see above) and calculations on the basis of data from elemental sulfur analyses indicated nearly equimolar amounts of 3HPTB, 3HPTHx, and 3HPTO.

TABLE 6

Some representative examples of substructures of poly(3HPTO-co-3HPTHx-co-3HPTB) according to negative ion ESI/MS and ESI/MS/MS analyses*

| Peak [m/z] [M-H—$H_2O$] | DP | Possible substructures |
|---|---|---|
| 159 | 1 | 3HPTB |
| 187 | 1 | 3HPTHx |
| 215 | 1 | 3HPTO |
| 319 | 2 | (3HPTB-3HPTB) |
| 375 | 2 | (3HPTO-3HPTB); (3HPTB-3HPTO); (3HPTHx-3HPTHx) |
| 535 | 3 | (3HPTO-3HPTB-3HPTB); (3HPTB-3HPTO-3HPTB); (3HPTB-3HPTB-3HPTO); (3HPTHx-3HPTHx-3HPTB); (3HPTHx-3HPTB-3HPTHx); (3HPTB-3HPTHx-3HPTHx) |

*Abbreviations: M, molecular weight of uncharged molecule; DP, degree of polymerization; 3HPTB, 3-hydroxypropylthiobutyrate; 3HPTHx, 3-hydroxypropylthiohexanoate; 3HPTO, 3-hydroxypropylthiooctanoate.

Discussion

Figure 6:
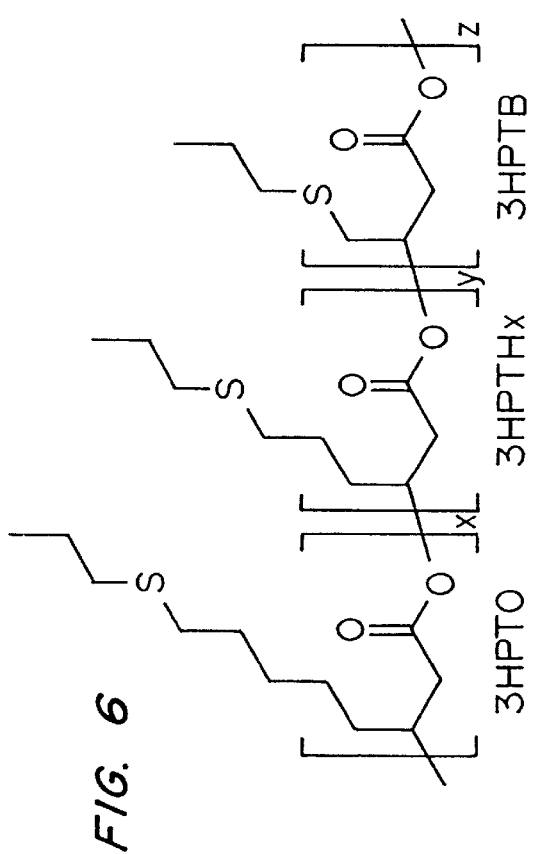
FIG. 6 is the structural formula of poly(3HPTB-co-3HPTHx-co-3HPTO).

Biosynthesis of a type of PHA bearing thioether groups. Using a metabolically engineered bacterium, biosynthesis of a sulfur containing PHA was achieved. This PHA consisted of 3-hydroxy-S-propyl-ω-thioalkanoates, and the structural formula of poly(3HPTB-co-3HPTHx-co-3HPTO) is shown in FIG. 6. The occurrence of thioether groups in the side chains reveals possibilities for chemical modifications or crosslinking of the PHA molecules, and provides putative technical applications of these biopolymers, e.g. in medicine and/or pharmacy.

If pseudomonades were cultivated with ATAs, a smell characteristic for alkylthiols occurred which contained an odd number of carbon atoms in the carboxylic acid part of the molecule such as PTUD or BTV. This indicates a spontaneously occurring cleavage of the 3-hydroxy-S-alkyl-ω-thiopropionyl-CoA into malonic acid semialdehyde CoA and the alkylthiol, whose further metabolic fate remains to be elucidated (Skrede et al. 1997).

In contrast, ATAs containing even numbers of carbon atoms in the carboxylic acid part of the molecule are presumably catabolized via the β-oxidation route to acetyl-CoA until the sulfur atom prevents another β-oxidation cycle. According to Skrede et al. (1997), the sulfur is metabolized to a sulfoxide, and further oxidation from the ω-end is most likely to occur.

The PHA-negative strain of R. eutropha PHB-4 was not able to synthesize poly(3HPTO-co-3HPTHx-co-3HPTB), confirming that a PHA synthase is involved in the synthesis of the PHAs. Since this strain is also not able to synthesize any other PHA, a recombinant strain of PHB⁻4 expressing the type-II PHA synthase of P. mendocina, which exhibited a broad substrate range like $PHA_{MCL}$ synthases of other pseudomonades, was chosen as candidate for the production of these PHAs. The broad substrate range of PHA synthases and in particular of type-II PHA synthases for substrates of different carbon chain length, which allows also the incorporation of hydroxyalkanoic acids containing various substituents at the alkyl moiety, is well known (Steinbüchel & Valentin, "Diversity of microbial polyhydroxyalkanoic acids" in *FEMS Microbiol Lett* 128:219–228 (1995))

We claim:

1. A biopolymer comprising thioester or thioether linkages and having monomeric units of the formula selected from the group consisting of:

[OC(R¹R²)C(R³R⁴)CO]$_x$—[S-C((R⁵R⁶)C(R⁷R⁸)CO]$_y$ FORMULA I and

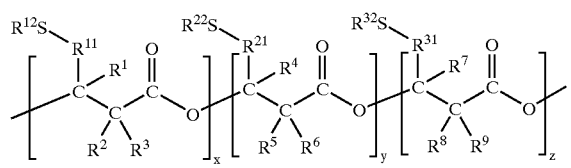

Formula II wherein, if the monomeric unit is one of formula I, x and y are integers which are independently between 1 and 15; and $R^1$, $R^2$, $R^3$, $R^4$, $R^5$, $R^6$, $R^7$, and $R^8$ are independently selected from hydrogen, methyl, $C_{2-15}$ straight, branched or cyclic alkyl, alkenyl or alkynyl groups, alkaryl groups, aralkyl groups, heteroalkyl groups, heteroaryl groups, hydroxy groups, thiol groups, disulfides, ether groups, thiolether groups, ester groups, carboxylic acid groups, amine groups, amide groups, halogens, nitrogen-substituted radicals; and/or oxygen-substituted radicals; and Wherein, if the monomeric unit is one of formula II, x, y and z are integers which are independently between 0 and 15, with the proviso that x+y+z>1;

$R^1$, $R^2$, $R^3$, $R^4$, $R^5$, $R^6$, $R^7$, $R^8$ and $R^9$ are independently selected from hydrogen, methyl, $C_{2-15}$ straight, branched or cyclic alkyl, alkenyl or alkynyl groups, alkaryl groups, aralkyl groups, heteroalkyl groups, heteroaryl groups, hydroxy groups, thiol groups, disulfides, ether groups, thiolether groups, ester groups, carboxylic acid groups, amine groups, amide groups, halogens, nitrogen-substituted radicals; and/or oxygen-substituted radicals;

$R^{11}$, $R^{21}$, and $R^{31}$ are di-radical groups which are independently selected from substituted or unsubstituted methylene, $C_{2-15}$ straight, branched or cyclic alkyl, alkenyl or alkynyl groups, alkaryl groups, aralkyl groups, heteroalkyl groups, and heteroaryl groups; and $R^{12}$, $R^{22}$, and $R^{32}$ are independently hydrogen, methyl, $C_{2-15}$ straight, branched or cyclic alkyl, alkenyl or alkynyl groups, alkaryl groups, aralkyl groups, heteroalkyl groups, and heteroaryl groups.

2. The biopolymer of claim 1 having a molecular weight between 300 and $10^7$ Daltons.

3. The biopolymer of claim 1 having a molecular weight between 10,000 and 10,000,000 Daltons.

4. The biopolymer of claim 1 containing between 10 and 100,000 monomeric units.

5. The biopolymer of claim 1 containing between 100 and 30,000 monomeric units.

6. The biopolymer of claim 3 wherein the monomeric units are selected from the group consisting of 3-mercaptobutyrate, 3-mercaptopropionic acid, 3-hydroxybutyrate, 3-hydroxyvalerate, 3-hydroxyhexanoate, 3-hydroxyheptanoate, 3-hydroxyoctanoate, 3-hydroxynonanoate, 3-hydroxydecanoate, 3-hydroxyundecanoate, 3-hydroxydodecanoate, 3-hydroxypropylthioundecanoic acid, 3-hydroxypropylthiooctanoic acid, 3-hydroxypropylthiohexanoic acid, 3-hydroxypropylthiobutyric acid, 3-hydroxypropylthiopropionic acid, 3-hydroxybutylthiovaleric acid, and 3-hydroxyoctylthiohexanoic acid units.

7. The biopolymer of claim 1 produced by bacterial fermentation.

8. A pharmaceutical composition comprising the biopolymer of claim 1.

9. The pharmaceutical composition of claim 8 wherein the biopolymer of claim 1 is used as an agent selected from the group consisting anti-bacterial agents, anti-viral agents, and anti-fingal agents.

10. The pharmaceutical composition of claim 9 wherein the biopolymer is used as an anti-bacterial agent.

11. The pharmaceutical composition of claim 10 wherein the composition is in the form of antibacterial coating.

12. A composition comprising the biopolymer of claim 1 wherein the composition is used as electrolyte.

* * * * *